United States Patent [19]
Roberts et al.

[11] Patent Number: 5,820,618
[45] Date of Patent: *Oct. 13, 1998

[54] WINGED SANITARY NAPKIN HAVING BARRIER MEANS

[75] Inventors: John David Roberts, West Chester, Ohio; Claude Paul Mancel, Waterloo, Belgium

[73] Assignee: The Procter & Gamble Company, Cincinnati, Ohio

[*] Notice: The term of this patent shall not extend beyond the expiration date of Pat. No. 5,542,941.

[21] Appl. No.: 892,713

[22] Filed: Jul. 15, 1997

Related U.S. Application Data

[63] Continuation of Ser. No. 307,672, filed as PCT/US93/02448 Mar. 15, 1993, Pat. No. 5,649,917.

[30] Foreign Application Priority Data

Mar. 31, 1992 [EP] European Pat. Off. .............. 92870052

[51] Int. Cl.[6] ........................................... A61F 13/15
[52] U.S. Cl. ........................................ 604/385.1; 604/387
[58] Field of Search ................. 604/385.1–387, 604/358, 378, 389

[56] References Cited

U.S. PATENT DOCUMENTS

| | | | |
|---|---|---|---|
| 4,589,876 | 5/1986 | Van Tillburg | 604/385.1 |
| 5,234,422 | 8/1993 | Sneller et al. | 604/385.2 |
| 5,391,162 | 2/1995 | Widlund et al. | 604/385.2 |
| 5,542,941 | 8/1996 | Morita | 604/385.2 |
| 5,618,283 | 4/1997 | Yamamoto | 604/387 |
| 5,649,917 | 7/1997 | Roberts et al. | 604/385.1 |

FOREIGN PATENT DOCUMENTS

| | | | |
|---|---|---|---|
| 557047 | 8/1993 | European Pat. Off. | 604/387 |
| 5552758 | 4/1980 | Japan | 604/385.1 |
| 5220191 | 8/1993 | Japan | 604/387 |
| 2244653 | 12/1991 | United Kingdom | 604/387 |
| 2263622 | 8/1993 | United Kingdom | 604/385.2 |

OTHER PUBLICATIONS

Translation of JP 5,552,758, Apr. 1980 Tsuchinori et al.

*Primary Examiner*—Mark O. Polutta
*Attorney, Agent, or Firm*—Steven W. Miller; E. Kelly Linman; Jacobus C. Rasser

[57] ABSTRACT

A sanitary napkin is provided with a barrier means to provide a barrier against lateral migration of body fluids. The barrier means can be provided on a sanitary napkin which has no wings and comprises in this core a distal edge which is located within the perimeter of the absorbent core during use of the sanitary napkin. The barrier means can also be provided on a sanitary napkin having wings and can be formed of a unitary part of the napkin's topsheet or can be formed by a separate strip of material.

12 Claims, 5 Drawing Sheets

Fig. 10

WINGED SANITARY NAPKIN HAVING BARRIER MEANS

This is a continuation of application Ser. No. 08/307,672, filed on Sep. 22, 1994, now U.S. Pat. No. 5,697,917; which is a 371 of PCT/US 93/02448 filed on Mar. 15, 1993.

FIELD OF THE INVENTION

The invention relates to a sanitary napkin comprising an absorbent core having a first face, a second face, a perimeter comprising two longitudinal sides and two lateral sides, a liquid-pervious topsheet overlaying the first face of the core, a liquid-impervious backsheet associated with the topsheet, the backsheet overlying the second face of the core, and barrier means located along the longitudinal sides for restricting liquid migration in a direction generally parallel to the lateral sides.

BACKGROUND OF THE INVENTION

Such a sanitary napkin is known from the British patent application GB 2 168 253.

In this patent application, the barrier means are located outside the perimeter of the core and are formed by an elasticised upstanding part of the topsheet and the backsheet. While lateral liquid migration is reduced by the barrier means, the rate of absorption of liquid entrapped between the barrier means and the core may be reduced. The known sanitary napkin may also undergo a shift in position during use.

It is an object of the invention to provide for barrier means in a sanitary napkin which are comfortable during use, which effectively restrict lateral spread of body fluids and which allow adequate absorption.

It is another object of the invention to provide a sanitary napkin which can be reliably positioned with respect to a user's undergarment.

SUMMARY OF THE INVENTION

A sanitary napkin according to the invention is characterized in that the barrier means comprise a wall having a free edge which is elevated above the plane of the first face of the core, the free edge being, at least during use of the sanitary napkin, located within the perimeter of the core.

By placing the barrier means so that at least the free edge is during use located on top of the absorbent core, instead of beside it, the liquid that is stopped by the barrier means from laterally spreading along the topsheet, is readily absorbed by the core.

Another absorbent article according to the invention is characterized in that the backsheet extends beyond the perimeter of the core to form flaps for attachment to a garment during use, the barrier means comprising a wall that is connected to the flaps adjacent the perimeter of the core.

The flaps can fold upward around the edge of an undergarment of the wearer, as is disclosed in U.S. Pat. No. 4,687,478 which is hereby incorporated by reference. It was found, that the flaps in combination with the barrier means provide for reduced lateral migration of body fluids. The barrier means can be formed by a liquid-impermeable wall or by an absorbent strip which is connected, for instance by gluing or by fusion bonding, to the flaps. The free edge of the wall is preferably located within the perimeter of the core during use of the sanitary napkin for effective absorption of the body fluids that are retained by the wall. It is however also possible that the fee edge of the wall is located outside the perimeter of the core, or, for instance when a shaped core is used, is located within the perimeter of the core for the broader parts of the core only.

An embodiment of an absorbent article according to the invention is characterized in that the wall is forned by a spacing member located between the topsheet and the backsheet.

The spacing member can be formed by a cantilever of flexible material that is placed between the topsheet and the backsheet outside the perimeter of the core and that presses the topsheet upwards. During use of the sanitary napkin, the napkin is compressed in a direction of the lateral sides and the topsheet is lifted by the cantilever. Preferably the free edge of the wall that is formed by the topsheet and the cantilever is pressed within the perimeter of the core during use of the sanitary napkin, to provide a good absorption of body fluids retained by the cantilever.

The barrier means can also comprise a foam strip which is glued, or otherwise connected, between the topsheet and the core or which is glued on top of the topsheet.

Another embodiment of an absorbent article according to the invention is characterized in that the barrier means comprises the topsheet, the topsheet having a central part overlaying the core and marginal parts forming the wall along the longitudinal sides of the core.

Even though the topsheet is fluid-pervious, the barrier means cause restriction of lateral spread of body fluids. Use of the topsheet to form the wall reduces the need for a separate barrier means and hence keeps the number of components used in the sanitary napkin low, which is desirable during manufacturing. The barrier means can extend along the whole of the perimeter of the core to also prevent fluid migration in a general direction of the longitudinal sides.

Preferably the free edge of the barrier means is contracted before use, so that during use the barrier means is stretched and is pulled away from the topsheet to stand up. The contraction can be caused by the application of an elastic member in its pre-stretched state along the free edge of the barrier means. The free edge of the barrier means, which can be formed by either the topsheet, the backsheet or the combination thereof, can also be crimped by application of heat to shorten the free edge of the barrier means. Shortening of the free edge in this way will also make the barrier means stand up upon longitudinally stretching the sanitary napkin during use.

BRIEF DESCRIPTION OF THE DRAWINGS

Some embodiments of a sanitary napkin according to the invention will be described in detail with reference to the accompanying drawings. In the drawings.

Figure 1:
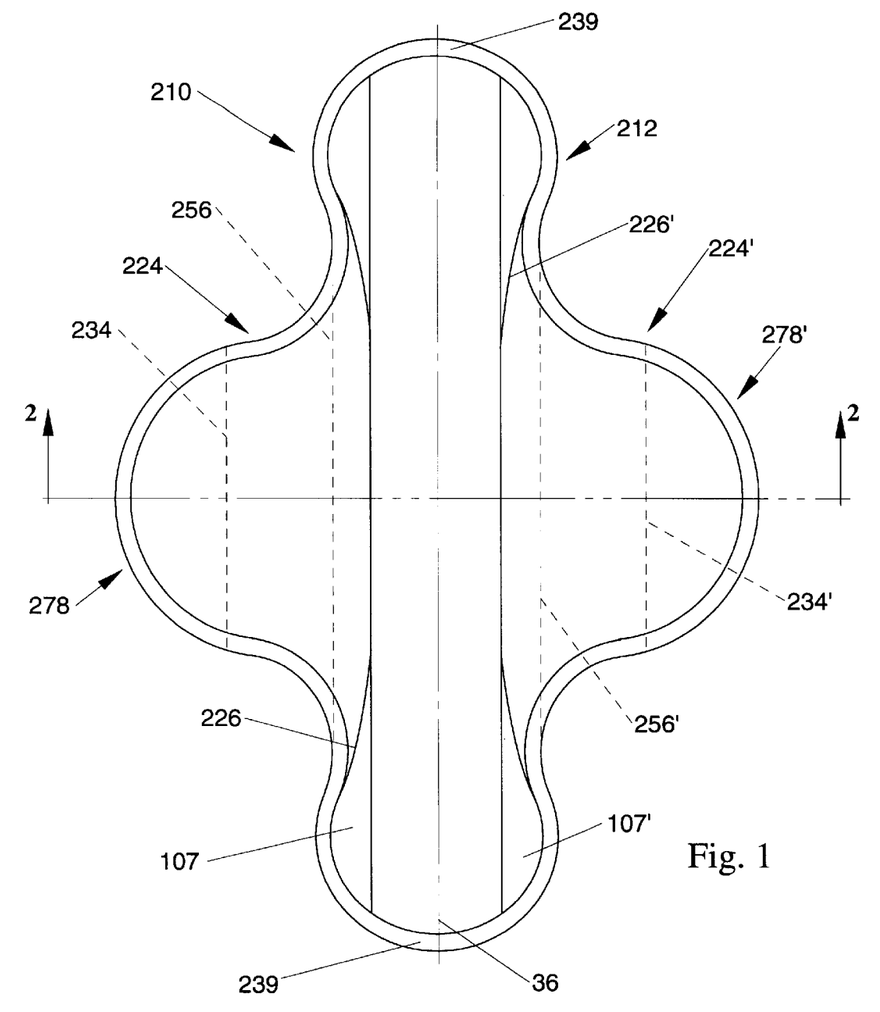
FIG. 1 is a plan view of a sanitary napkin of the present invention.
Figure 2:
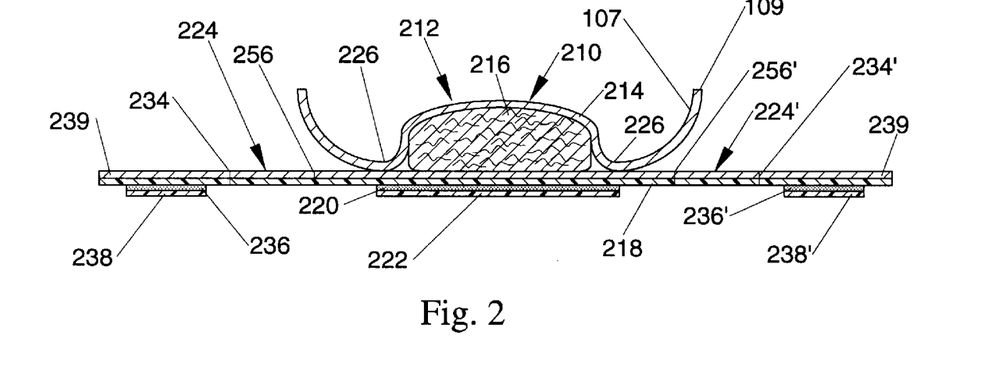
FIG. 2 is a cross sectional view of the sanitary napkin of FIG. 1 along the line 2—2 of FIG. 1, the barrier means being formed by the topsheet.

A preferred embodiment of a sanitary napkin of the present invention is shown in FIGS. 1 and 2. Sanitary napkin 210 comprises an absorbent means represented by central absorbent pad 212 and two flaps 224 and 224'. (In the discussion that follows, unless otherwise noted, the sanitary napkins will have two flaps. While it is not necessary that the flaps be identical, or, more properly, mirror images one of the other, they preferably are. Thus the description of the first will be a description of the second. Discussion of the second will, therefore, be omitted for clarity of exposition. Corresponding elements are indicated in the drawings by reference numerals and primed reference numerals).

Flap 224 is associated with central absorbent pad 212 along nonlinear line of juncture 226. As used in the context of the present specification, the term "nonlinear" refers to any of various curved, as opposed to straight, lines.

Flap 224 has distal edge 278 which is remote from line of juncture226. In the embodiment illustrated in FIG. 1, line of juncture 226 is concave relative to distal edge 278. That is to say, line of juncture 226 curves away from distal edge 278. In this embodiment, nonlinear lines of juncture 226 and 226' and seam 239 define an absorbent means (central absorbent pad 212) which is narrower in-its central region that at its ends. A sanitary napkin narrower in the center than at the ends is generally perceived by the user as more comfortable than a sanitary napkin of uniform width.

Flap 224 is provided with first imaginary axis of flexibility 256 and second axis of flexibility 234.

FIG. 2, a cross sectional view of sanitary napkin 210 taken along line 2—2, illustrates generally the preferred construction for sanitary napkin 210. As shown in FIG. 2, central absorbent pad 212 comprises absorbent core 216. Central absorbent pad 212 and flap 224 both comprise topsheet 214. Backsheet 218 is disposed on the side of absorbent core 216 and flap 224 opposite that of topsheet 214. In effect, topsheet 214 forms one surface of flap 224 while backsheet 218 forms the other surface; topsheet 214 also forms one surface of central absorbent pad 212, backsheet 218 the other.

In the embodiment illustrated, flap absorbent core 230 is interposed between topsheet 214 and backsheet 218. For simplicity of construction, flap absorbent core 230 extends throughout napkin 210 and is interposed between absorbent core 216 and backsheet 218. While this is a preferred embodiment primarily for reasons of construction, it is not necessary that flap absorbent core 230 be interposed between absorbent core 216 and backsheet 218.

Topsheet 214 and backsheet 218 are joined at seam 239 around the entire periphery of sanitary napkin 210. The purpose of this seam is to unite the various elements of the sanitary napkin into a whole. Topsheet 214 is secured to flap absorbent core 230 and backsheet 218 along nonlinear lines of juncture 226 and 226' by attachment means not illustrated in FIG. 2.

Illustrated in FIG. 2 are the adhiesive attachment means central pad adhesive 220 and flap adhesive 236 which are covered by, respectively, central pad release liner 222 and flap release liner 238. These adhesive attachment means are adapted to secure sanitary napkin 210 within the crotch region of an undergarment.

Topsheet 214 is liquid permeable and, when sanitary napkin 210 is in use, is in close proximity to the skin of the user. Topsheet 214 is compliant, soft feeling and non-irritating to the user's skin. It can be made from any of the materials conventional for this type of use. Non-limiting examples of suitable materials that can be used as topsheet 214 are woven and nonwoven polyester, polypropylene, nylon, and rayon and formed thermoplastic films; formed films are preferred. Suitable formed films are described un U.S. Pat. No. 4,324,246 issued to Mullane and Smith on Apr. 13, 1982 and U.S. Pat. No. 4,342,314 issued to Radel and Thompson on Aug. 3, 1982, both of which patents are incorporated herein by reference. Formed films are preferred for topsheet 214 because they are pervious to liquids and yet non-absorbent. Thus, the surface of the formed film, which is in contact with the body, remains dry and is more comfortable to the wearer.

In preferred embodiments of the present invention, the outer surface of topsheet 214 is treated with a surfactant. Treating the outer surface of the topsheet with surfactant renders the surface more hydrophilic which results in liquid penetrating the topsheet faster than if the surface were not treated. This diminishes the likelihood that menstrual fluid will flow off topsheet 214 rather than being absorbed by the absorbent core 216. It is preferred that the surfactant be substantially evenly and completely distributed across the outer surface of topsheet 214. This can be accomplished by any of the common techniques well known to those skilled in the art. For example, the surfactant can be applied to topsheet 214 by spraying, by padding, or by the use of transfer rolls.

In preferred embodiments, the inner surface of topsheet 214 is secured in contacting relating to absorbent core 216. This contacting relationship results in liquid penetrating topsheet 214 faster than if it were not in contact with absorbent core 216. Topsheet 214 can be maintained in contact with absorbent core 216 by applying adhesive, preferably in spaced, limited areas, to the inner surface of the topsheet 214. Examples of suitable adhesives used for this purpose include the acrylic emulsion E-1833BT manufactured by Rohm and Haas Company of Philadelphia, Pa. and the acrylic emulsion WB3805 manufactured by H. B. Fuller Company of St. Paul, Minn. The adhesives can be applied by the same methods as the surfactant is applied to the outer surface of topsheet 214.

Referring to FIG. 2, it can be seen that absorbent core 216 is positioned between topsheet 214 and backsheet 218. Absorbent core 216 provides the means for absorbing menstrual fluid. Absorbent core 216 is generally compressible, conformable, and non-irritating to the user's skin. It can comprise any material used in the art for such purpose. Examples of suitable materials are layers of tissue (such as wadding) and fibrated comminution pulp (airfelt), with fibrated comminution pulp being preferred.

Backsheet 218 is impervious to liquids and, thus, prevents menstrual fluid which may be expressed from absorbent core 216 from soiling the clothing of the user. Any material used in the art for such purpose can be utilized herein. Suitable materials are embossed or nonembossed polyethylene films and laminated tissue.

The outer surface of backsheet 218, generally in register with absorbent core 216, is coated with central pad adhesive 220. Central pad adhesive 220 provides an adhesive attachment means for securing central absorbent pad 212 in the crotch portion of a panty. Any adhesive or glue used in the art for such purpose can be used herein, with pressure sensitive adhesives being preferred. Suitable adhesives are Century A-305-IV manufactured by the Century Adhesives Corporation and Instant Lok 34-2823 manufactured by National Starch Company. As shown in FIG. 2, central pad adhesive 220 is generally the same width as absorbent core 216; the width is not critical and appropriate widths, as well as lengths, can be readily selected by those skilled in the art. The pressure sensitive adhesive of central pad adhesive 220 should be covered with central pad release liner 222 to keep the adhesive from drying out and to keep it from sticking to extraneous surfaces prior to use. Any commercially available release liner commonly used for such purposes can be used herein. Nonlimiting examples of suitable release liners are BL 30 MG-A Silox E1/0 and BL 30 MG-A Silox 4 P/O both of which are manufactured by the Akrosil Corporation.

As can be observed from the foregoing discussion, central absorbent pad 212 is an absorbent means that has a fluid pervious body contacting surface (represented in FIG. 2 by topsheet 214) and an opposed liquid impervious surface (represented bin FIG. 2 by backsheet 218). It is to be understood that the embodiment illustrated in only one possible embodiment, albeit a preferred one. Other possible embodiments include one in which an absorbent core is essentially completely wrapped with topsheet before it is placed on a backsheet. The absorbent means can also comprise an absorbent core which possesses sufficient integrity to stand alone and which is fluid permeable on one surface while the other surface has been treated to render it liquid impervious.

It should be noted that a narrow central absorbent pad 212 is effective because the overall configuration and use of sanitary napkin 210 results in central absorbent pad 212 being maintained in close proximity to the body. Such proximity of central absorbent pad 212 places it precisely where it should: very near the body at the vaginal opening. Central absorbent pad 212 can then absorb the vast majority of the menstrual fluid (menses) before it has an opportunity to flow along central absorbent pad 212.

It is to be observed that lines of juncture 226 and 226' are the lines along which flaps 224 and 224' are associated with the absorbent means (represented by central absorbent pad 212); as such they represent lines of demarcation between the absorbent means and the flaps. It is also to be observed that the lines of juncture are nonlinear in this embodiment, but can also be straight. Preferably, they are concave relative to distal edges 278 and 278' and relative to the bulk of central absorbent pad 212. The absorbent means thus takes on a shape in which the width at its center is less than the width at its ends. This contoured shape is closely attuned to anatomical dimensions of the crotch region of the user. It makes the sanitary napkin more comfortable to wear while, at the same time, making it more effective as by rendering it less subject to compression by the legs of the user. While nonlinear lines of juncture which are convex relative to the distal edges and to the bulk of the central absorbent pad can be used, they are not preferred.

It is preferred that the width of central absorbent pad 212 between lines of juncture 226 and 226' at their nearest approach be from about 1 to about 8 centimeters. The width of the central absorbent pad 212 at its ends should be from about 2 to about 9 centimeters. Central absorbent pad 212 should be from about 7.6 to about 38 centimeters long.

Central absorbent pad 212 need not have an absorbent capacity much greater than the total amount of menstrual fluid anticipated to be absorbed. Thus, central absorbent pad 212, in addition to being narrow, can be relatively thin. Furthermore, a narrow and thin absorbent means is extremely comfortable to the user. In the embodiment illustrated in FIGS. 1 and 2, topsheet 214 does not serve as a topsheet for flaps 224 and 224'. In general, the flaps do not require a topsheet to enable them to function properly, but the use of a topsheet is preferred. Flap topsheets can be integral with the absorbent means' body contacting surface or they can be independent elements as illustrated; the former is preferred. All the specific physical property comments made above about topsheet 214 apply to any flap topsheet that is used. There is, however, no requirement that the flap topsheet be the same material as the topsheet associated with the central absorbent pad. In preferred embodiments, the flap topsheet can be a nonwoven material while the topsheet with the central absorbent pad is a formed film.

In the embodiment illustrated in FIGS. I and 2, backsheet 218 serves as a backsheet for flaps 224 and 224'. The flaps require a backsheet (or more generally, a liquid impervious material) to enable them to function properly. The flap backsheets can be integral with the absorbent means liquid impervious surface, as illustrated, or they can be independent element; the former is preferred. All the specific physical property comments made above about backsheet 218 apply to any flap backsheet.

The overall size of flap 224 can be readily selected by those skilled in the art. Preferably, sanitary napkin 210 is from about 10 to about 23 centimeters wide between distal edges 278 and 278' at their greatest separation. Preferably flap 224 is from about 7.6 to about 18 centimeters long in the direction parallel to the longitudinal axis of the sanitary napkin.

The outer surface of flap 224, adjacent distal edge 278, is coated with flap adhesive 236.

Flap adhesive 236 is an adhesive attachment means which is used to assist in maintaining flap 234 in position after it is wrapped around the edge of the crotch portion of a panty as described below. Any adhesive used for central pad adhesive 220 can be used as flap adhesive 236. Also, flap adhesive 236 is covered with a removable flap release liner 238. Any release liner material used for central pad release liner 222 can be used for flap release liner 238.

As shown in FIGS. 1 and 2, topsheet 214 is secured to backsheet 218 along seam 239. Seam 239 can be formed by any means commonly used in the art for this purpose such as by gluing, crimping or heat sealing.

Seam 239 is illustrated extending completely around the periphery of sanitary napkin 210; this is a preferred embodiment for ease of construction. (Other means of uniting the various elements of the device can be used).

Topsheet 214 can be secured to backsheet 218 along lines of juncture 226 and 226' by any of the techniques used to form seam 239.

Flap 224 contains first axis of flexibility 256 and second axis of flexibility 234. These two axes of flexibility allow flap 224 to form a wall, in use, as described hereinafter. The axis of flexibility can be formed by a separate hinge line or can be located along a continuous range in the flap 224, which is as flexible so as to bend around any desired line.

First axis of flexibility 256 is so constructed as to allow the flap to bend along first axis of flexibility 256. The direction of the bend of the flap is upward when sanitary napkin 210 is in the configuration of FIG. 2. More generally, the direction of the bend is such that that portion of flap 224 containing distal edge 278 rotates about the first axis of flexibility 256 in an arc beginning generally from its extended position, as shown in FIG. 2, toward the fluid pervious body contacting surface of the absorbent means (as represented in FIG. 2 by that portion of topsheet 214 in register with absorbent core 216) and away from the liquid impervious surface of the absorbent means (as represented in FIG. 2 by that portion of backsheet 218 in register with absorbent core 216).

Second axis of flexibility 234 is so constructed as to allow the flap to bend along second axis of flexibility 234. The direction of the bend is downward when sanitary napkin 210 is in the configuration of FIG. 2. More generally, the direction of the bend is such that that portion of the flap 224 containing distal edge 278 rotates about second axis of flexibility 234 in an arc generally from its extended position, as shown in FIG. 2, toward the liquid impervious surface of the absorbent means (as represented in FIG. 2 by that portion of backsheet 218 in register with absorbent core 216 as comprising central absorbent pad 212) and away from the fluid pervious body contacting surface of the absorbent means (as represented in FIG. 2 by that portion of topsheet 214 in register with absorbent core 216).

First and second axes of flexibility can be provided in various ways. A preferred method is shown in FIGS. 1 and 2. In the embodiment illustrated, the materials of construction of flap 224 are selected so that flap 224 is extremely flexible over essentially the whole of its extent. Axes of flexibility of 256 and 234, as shown in FIGS. 1 and 2, are not, then, single, unique structures, but are, rather, representative of an essentially infinite number of pairs of axes. This arrangement is particularly preferred because it allows sanitary napkin 210 to be easily adjusted, during application, to properly fit a number of differently sized undergarments and, in use, anatomies of described below.

Total flexibility of flap 224 permits flap 224 to be positioned around the edge of the crotch portion of a panty without having to alter the natural path of the edge of the crotch portion of a panty. thus, the edge of the crotch portion of a panty need not be stretched to fit to the second flexible axis of the flap. Furthermore, the natural path of the edge of the crotch portion of a panty results, when the sanitary napkin is in place for use, in the highest wall (described below) being formed; this, in turn, provides the greatest barrier to flow of the menstrual fluid.

In the embodiment of sanitary napkin 210 illustrated in FIGS. 1 and 2, it is preferred that the materials of construction of flap 224 be selected so that the flap has a resistance to bending, through an arc of 90° C., of less than about 200 grams, more preferably less than about 50 grams, and most preferably less than about 25 grams as measured by the PCA Score Bend Tester manufactured by the Thwing-Albert Instrument Company of Philadelphia, Pa. These values are obtained when a section of flap 7.6 centimeters long (and which is maintained 2.5 centimeters above the bottom edge of the tilting plate of the tester) is evaluated under TAPPI standard conditions.

In the abstract, an axis is generally considered to be a linear element. The present axes of flexibility are also generally linear, but, since the materials from which the flaps are constructed generally possess such a degree of flexibility that the flaps can be bent and folded conveniently with manual force, the axes of flexibility can become nonlinear under the influence of external forces.

As illustrated in FIG. 1, first axis of flexibility 256 is in close proximity to line of juncture 226. First axis of flexibility 256 can, in fact, intersect the line of juncture 226 at the point the latter contacts the outer margin of the sanitary napkin (as that margin is represented by seam 239). In the general case, this will be the only situation in which first axis of flexibility 256 and line of juncture 226 touch or coincide. It is to be understood, however, that application of external forces during use can cause the first axis of flexibility to be displaced toward the line of juncture so that, in some instances, the two can touch or coincide.

Sanitary napkins including the central absorbent pad comprising a liquid pervious topsheet, a liquid impervious backsheet, and an absorbent core interposed between the topsheet and the backsheet, and having a flap extending from each longitudinal edge of the central absorbent pad, wherein the line of juncture between each flap and the longitudinal edge of the central absorbent pad is linear, and having each flap provided with a flexible axis located in the body of the flap, can be constructed so that the sanitary napkin preferentially bends at the linear line of juncture of each flap and the longitudinal edge of the central absorbent pad as well as at the flexible axis located within the body of the flap. Such napkins, while distinctly different from those of the present invention, will function in a manner analogous to those of the present invention.

The precise shape of flap 224, as well as the overall shape of sanitary napkin 210, can be selected by those skilled in the art without undue experimentation. In the embodiments illustrated in FIGS. 1 and 3, the flaps are symmetrically disposed along the longitudinal axis of the sanitary napkin; while this is a preferred embodiment, it is not a mandatory design feature. As noted above, the flaps are generally mirror images one of the other; while such a situation is preferred, it is likewise not a mandatory design condition.

Further, the sanitary napkins illustrated in FIGS. 1 and 2 are embodiments wherein the flaps are formed integrally with the topsheet sand backsheets of the sanitary napkin. Once again, while this is a preferred method of construction, it is not mandatory. Flaps and central absorbent means can be formed independently and joined by techniques well known to those skilled in the art in such a manner that the resulting sanitary napkin will function essentially equivalently to the embodiments illustrated herein.

In use, the sanitary napkins of this invention can be held in place by any support means well known for such purpose. Belts worn about the waist of the user can be used. It is highly preferred, however, that they be placed in the user's panty undergarment as described below.

Figure 8:
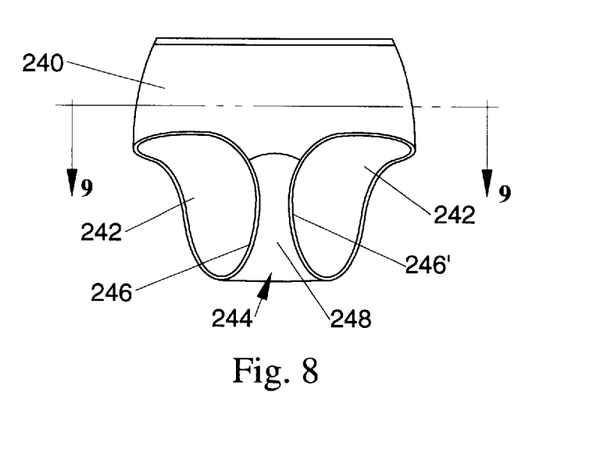
FIG. 8 is a front view of a conventional panty in which a sanitary napkin according to the invention can be used.

FIG. 8 is an undergarment of the type commonly worn by many women and well known as a panty. It comprises front section 240, back section 242, and crotch portion 244 which joins front and back sections 240 and 242. Crotch portion 244 comprises two side edges 246 and 246' and center crotch portion 248.

Figure 9:
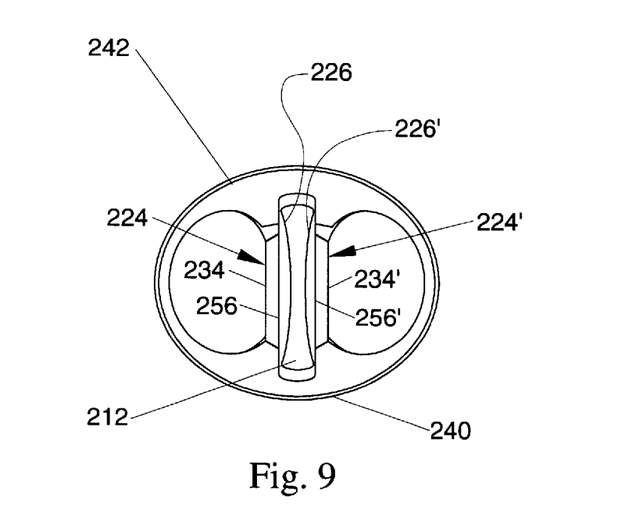
FIG. 9 is a cross sectional view of the panty of FIG. 8 taken along line 6—6 showing the sanitary napkin of FIG. 1 disposed therein and FIG. 10 is a fragmentary coronal view showing the sectioned sanitary napkin and panty of FIG. 8 in place on a user.

A sanitary napkin of the present invention, such as the one illustrated at 210 in FIGS. 1 and 2, is utilized by removing the release liners 222, 238 and 238' and thereafter placing the sanitary napkin in a panty as shown in FIG. 9. The center of central absorbent pad 212 is placed in crotch portion 244 of the panty with one end of central absorbent pad 212 extending toward front section 240 and the other end toward back section 242 of the panty and with backsheet 218 in contact with the inner surface of center crotch portion 248 of the panty. Central pad adhesive 220 maintains central absorbent pad 212 in position. The distal portions of flaps 224 and 224' are folded around, respectively, side edges 246 and 246' of the panty by bending along second flexible axes 234 and 234'. Flap adhesive 236 and 236' secure flaps 224 and 224' in such position. Thus, flaps 224 and 224' are each folded over themselves with a portion of the panty—including side edges 246 and 246'—interposed therebetween.

Numerous benefits are derived from the use of the sanitary napkin of the present invention. Flaps 224 and 224' are wrapped around each edge 246 and 246' of the crotch portion 244 of the panty as shown in FIG. 8. This encapsulation of the panty crotch assists in preventing the menstrual fluid from coming into contact with the center crotch portion of the panty. Thus, the center crotch portion of the panty will not be soiled.

There are two other benefits. One is that the portions of the flaps containing the second axes of flexibility, 234 and 234', provide an excellent gasket-like seal against the body. The other is that the central absorbent means, such as central absorbent pad 212, is maintained in excellent contiguous relationship to the body.

Figure 10:
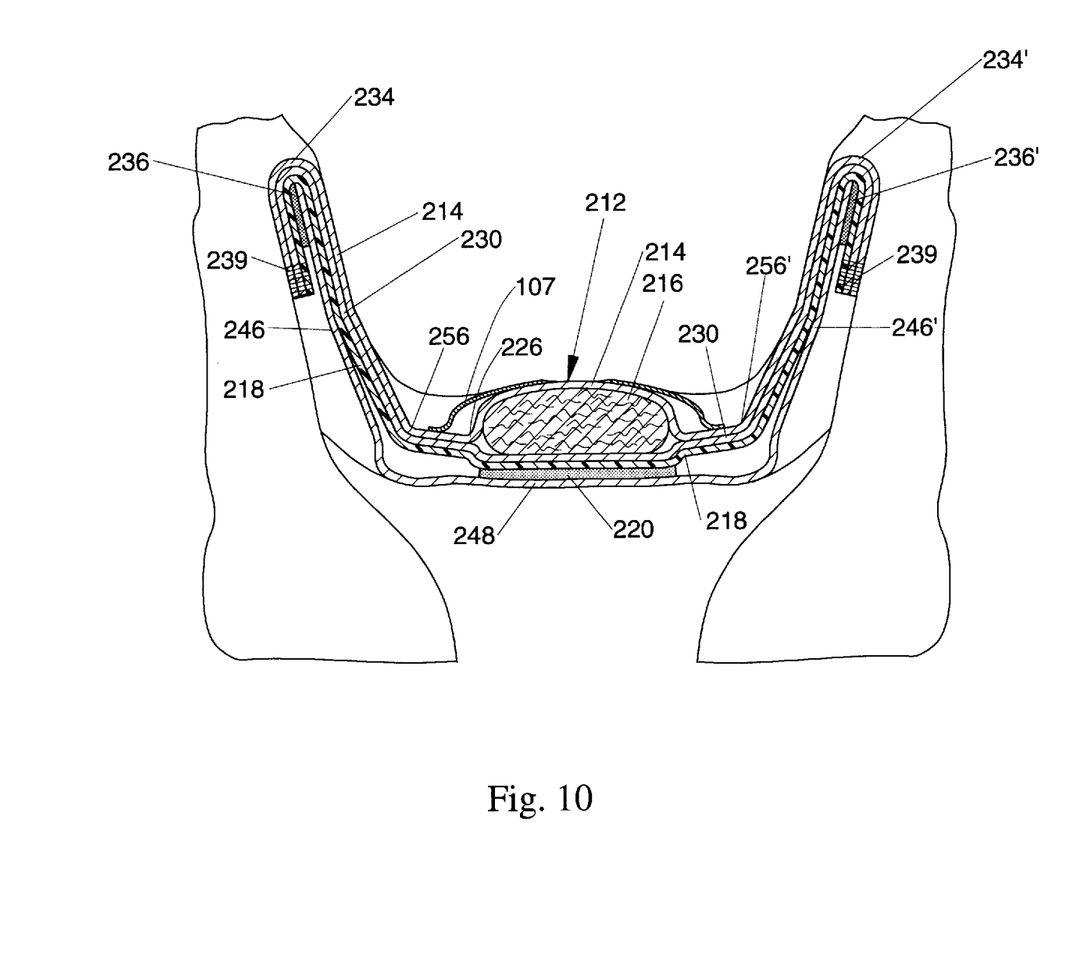

The edge of the crotch portion of a panty generally contains an elastic material. When a panty is worn, the elastic of the edge of the crotch portion generates an upward force, i.e. against the body, due to the energy in the elastic and the fit of the panty. The placement of the second axis of flexibility, such as second axes of flexibility 234 and 234', between the body and the edges of the crotch portion of the panty results in the upward force generated by the edge of the crotch portion of the panty pushing the portion of the flaps containing the second axes of flexibility snugly against the body. This results in a gasket-like-seal being formed along the axes of flexibility between the flaps and the body. This is illustrated in FIG. 10 which is a fragmentary coronal view showing the sectioned sanitary napkin and panty of FIG. 8 in place on a user. (A coronal view is the frontal plane that passes through the long axis of the body). The gasket-like seal assists in preventing menstrual fluid from penetrating beyond the second axis of flexibility which, in turn, minimizes soiling of the legs and adjoining clothing. Another benefit derived from the flaps being pushed snugly against the body along the second axes of flexibility is that the absorbent means (central absorbent pad) is forced into close proximity to and into conformity with the body. This, too, is illustrated in FIG. 10. The maintenance of the central absorbent pad against the body is known as "good body contact". Good body contact is beneficial because it provides a barrier to lateral flow of menstrual fluid. Without such a barrier, menstrual fluid would tend to flow quickly along the topsheet, thereby providing less time for it to be absorbed by the absorbent core.

Inherent bunching is the formation of wrinkles along the lateral axes of a sanitary napkin resulting from the initial placement of the sanitary napkin in a panty for use. (Lateral axes of a sanitary napkin extend across the "crotch portion" of the napkin generally parallel to line 2—2 of FIG. 1). This inherent bunching is due to the facts that a sanitary napkin is essentially linear along its longitudinal axis and that the anatomical contour of the body where the sanitary napkin is placed in essentially "U" shaped. (The longitudinal axis of a sanitary napkin extends from end to end of the central absorbent means and is generally perpendicular to line 2—2 of FIG. 1). Thus, as soon as a sanitary napkin is put in place, its shape is changed along its longitudinal axis from being essentially linear to "U" shaped. This change in shape creates wrinkles along the lateral axes of the sanitary napkin, with the vast majority of the wrinkles being at the point of greatest curvature of the body, i.e. the crotch area.

Forced bunching is the wrinkling of a sanitary napkin, along either its lateral or longitudinal axes, caused by movement of the legs of the user.

Wrinkles in a sanitary napkin created by inherent and forced bunching are known as flow channels because menstrual fluid can easily flow along the trough of the wrinkle in the absence of significant body contact along the wrinkle.

The sanitary napkin of the present invention provides numerous benefits because the flaps bend at the first axis of flexibility. In particular, the benefits provided are that:

(1) inherent bunching results in flow channels being formed substantially only in the central absorbent pad, not the bulk of the flaps;

(2) the sanitary napkin of the present invention can withstand much forced bunching before flow channels are created;

(3) even if the forced bunching is harsh enough to create flow channels, the channels formed will be essentially limited to the central absorbent pad; and (4) even if the forced bunching is so great that flow channels are created in both the central absorbent pad and the flaps, the menstrual fluid is restrained from penetrating beyond the second flexible axes of the flaps.

These four benefits are obtained because the sanitary napkin of the present invention is provided with barrier means or walls 107 and because it bends along the axes of flexibility. The anatomical features of the crotch area of a woman are such that the crotch section is substantially trapezoidal shaped, with the center area of the crotch, which is located at the vaginal opening, being the base of the trapezoid. When a sanitary napkin of the present invention, such as the embodiment shown in FIGS. 1 and 2, is in use, the anatomical features of the crotch area force the sanitary napkin to bend upward at the first axis of flexibility. This results in the sanitary napkin forming a wall at each side of the central absorbent pad; the wall extends from the first axis of flexibility to the second axis of flexibility, as illustrated in FIG. 10. Thus, in use, the sanitary napkin of the present invention has a well-like shape with the plane formed by the second axes of flexibility (234 and 234') that are wrapped around the edge of the crotch portion of the panty (246 and 246') being higher than the plane formed by the first axes of flexibility (256 and 256') when the user is in an upright position.

Inherent bunching in the sanitary napkin of the present invention is substantially limited to the central absorbent pad; essentially no flow channels are formed in the walls. Without being bound by any theory, it is believed that when the flow channels are being formed, the energy creating them is transmitted across the central absorbent pad and the flow channels are extended. This proceeds until the flow channels reach the first axes of flexibility. The flow channels extend no farther than this because, it is believed, the first axes of flexibility relieve the energy extending the flow channels. Thus the flow channels will not reach the gasket-like seal formed between the flap and the body at the second axis of flexibility, and, therefore, the seal will remain intact. The gasket-like seal forms a dam and blocks the flow of the menstrual fluid. The menstrual fluid can then be absorbed (or absorbed) by the absorbent core.

The sanitary napkin of the present invention can withstand much forced bunching before any flow channels are created, because the energy transmitted to the sanitary napkin by the forced bunching results in the walls tending to rotate around each first axis of flexibility. Without such rotation flow channels would be formed.

Even if the forced bunching is harsh enough to create flow channels, the channels will be substantially limited to the central absorbent pad. This is true for the same reasons that inherent bunching forms flow channels only in the central absorbent pad. Therefore, the gasket-like seal will remain intact and form a dam and block the flow of the menstrual fluid until it can be absorbed by the absorbent core.

Even if the forced bunching is so great that flow channels are created in both the central absorbent pad and the flaps, menstrual fluid is restrained from penetrating beyond the walls 107 and beyond the second axes of flexibility of the flaps. Such flow channels are likely to break the gasketlike seal. However, menstrual fluid is restrained from penetrating beyond the second flexible axes of the flaps because the walls themselves will form a barrier to flow of menstrual fluid. Menstrual fluid would have to flow up the walls, which is substantially directly against the force of gravity when the user is in an upright position, in order to penetrate the break in the gasket-like seal. Thus the walls themselves restrain the flow of the menstrual fluid.

In summary, the sanitary napkin of the present invention forms flow channels essentially only in the central absorbent pad which results in the gasket-like seal remaining intact. Thus, menstrual fluid will not flow beyond the gasket-like seal. However, if the forced bunching is so great that the gasket-like seal breaks, the walls themselves restrain the flow of the menstrual fluid.

It is important to note that in FIG. 10 flap adhesive 236 is illustrated as contacting the edge of the panty only on its "outer" surface. While this is a preferred way of securing the sanitary napkin in the panty, flap adhesive can contact the edge of the panty on only its "inner" surface or both its "inner" and "outer" surfaces so long as a portion of the flap extends around and about the edge of the panty.

The sanitary napkin of this invention has been described as a device which has two flaps which, in use, each form a wall. While those embodiments are highly preferred, devices not having flaps or having only one flap can be envisioned. This one flap would be associated with the central absorbent means along a nonlinear line of juncture. The flap would contain at least two, and preferably at least four, axes of flexibility which would allow it to form both walls described above as it is folded completely around the crotch portion of a panty. The flap would then be associated with the central absorbent means along a nonlinear line of juncture opposite the one mentioned above.

In the embodiments of the sanitary napkin of this invention, illustrated and discussed above, adhesive attachment means were present near the distal edges of the flaps and in register with the central absorbent pad. These elements, designed to hold the sanitary napkin securely in the crotch region of an undergarment, are highly preferred elements. Without detracting from that position, it can be asserted that embodiments of the present invention which effectively lack one or more of the described adhesive attachment means are also useful, novel, effective devices.

The embodiment illustrated in FIGS. 1 and 2 can be readily adapted to function as an embodiment of the present invention which is effectively free of one or more of the adhesive attachment means.

For example, central pad adhesive 220 (and, naturally, its associated central pad release liner 222) can be omitted from sanitary napkin 210 illustrated in FIGS. 1 and 2. In use, this modified embodiment would be placed in the interior crotch region of a panty, just as the unmodified embodiment, except that central absorbent pad 220 is not secured to the interior crotch region of the panty. Flaps 224 and 224' can be secured about the elastic edge of the panty as described above with flap adhesive 236 and 236'. The panty with its associated modified sanitary napkin would then be donned by the user as before. Flap adhesive 236 and 236' in cooperation with the elastic edges of the panty hold the modified sanitary napkin in place.

In a like manner, sanitary napkin 210 can be modified by omitting only flap adhesive 236 and 236' (and release liners 238 and 238'). The modified sanitary napkin would be secured in the crotch region of the panty with central pad adhesive 220 and the flaps would be merely folded about the elastic edges.

In a like manner, sanitary napkin 210 can be modified by omitting all flap and central pad adhesives. In use, such a modified sanitary napkin would be maintained in position solely by cooperation among the flaps, the elastic edges of the panty, and the user's body.

Figure 3:
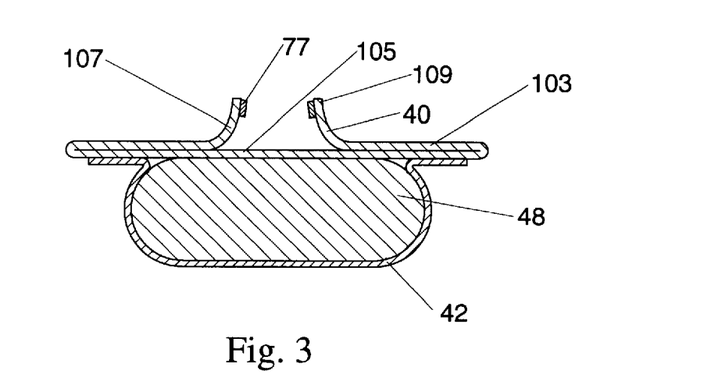
FIG. 3 is a cross sectional view of a sanitary napkin according to the invention, the barrier means being formed by the topsheet and located within the perimeter of the core.

FIG. 3 shows an embodiment wherein the topsheet 40 comprises a central pad 105 and is folded over at its marginal parts 103. At the perimeter of the core 48 the topsheet comprises two layers that are bonded together for instance by adhesive or ultrasonic fusion bonding. The free edge 109 of the wall 107 that is formed by the topsheet, is located on top of the absorbent core 48 within its perimeter that is defined by sides 226 and 226' as shown in FIG. 1. To the free edge 109 a contraction member is connected in the form of an elastic 77.

Figure 4:
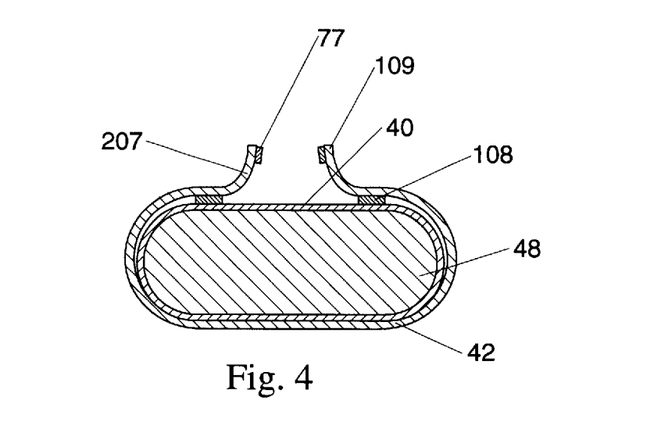
FIG. 4 is a cross-sectional view of an embodiment of a sanitary napkin according to the invention, the barrier means being formed by the backsheet.

In the embodiment of FIG. 4, the walls 107 are formed by the backsheet 42 that is wrapped around the core 48 and that is connected to the topsheet 40 in bond areas 108 at the top of the core.

Figure 5:
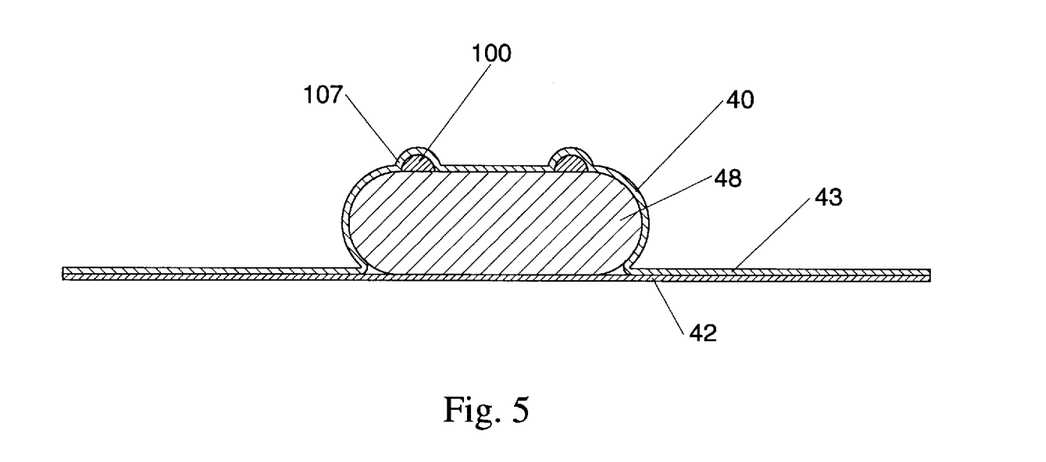
FIG. 5 is a cross-sectional view of an embodiment of a sanitary napkin, the barrier means being formed by a foam strip.

In the embodiment as shown in FIG. 5, the wall 107 is formed by a foam strip 100 which is located underneath the topsheet on top of the core 48. The sanitary napkin of FIG. 5 is provided with wings 43 for connection to a user's garment as shown in FIG. 10.

Figure 6:
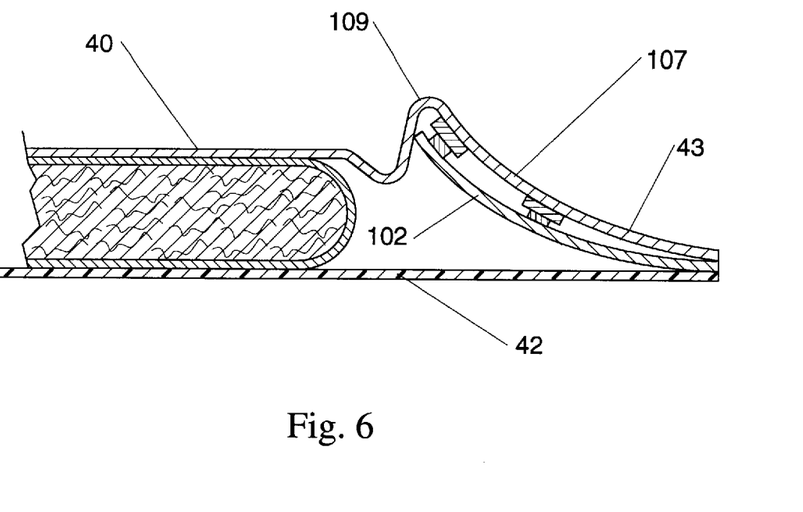
FIG. 6 is an embodiment of a sanitary napkin, the barrier means being formed by a cantilever.

In the embodiment of FIG. 6, the wall 107 is formed by a flexible cantilever 102 which is connected between the topsheet 40 and the backsheet 42.

Figure 7:
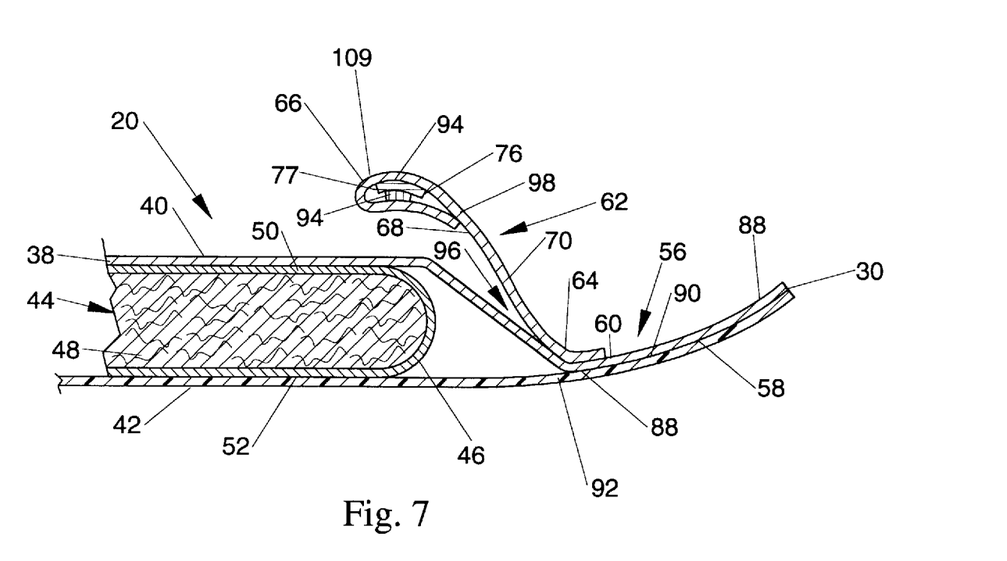
FIG. 7 is an embodiment of a sanitary napkin having flaps, the barrier means being formed by a strip which is glued to the flaps.

FIG. 7 is a fragmentary sectional view and depicts the construction in the crotch region of a further embodiment of a sanitary napkin according to the invention as it is shaped before being applied to the wearer (i.e. the napkin is subjected to elastic contraction). The absorbent core 44 comprises the absorbent layer 48 that is shown as being completely enveloped by the first and second tissue layers 50 and 52. The absorbent core 44 is disposed between the topsheet 38 and the backsheet 42, both the topsheet 38 and the backsheet 42 extend beyond the side edge 46 of the absorbent core 44 to define the side flap 58. The juxtaposed areas of the topsheet 38 and the backsheet 42 are adhesively secured together by adhesive 88.

The barrier means 62 is shown as being formed by securing an element to the topsheet 38 between the flap's outer edge and the side edge 46 of the absorbent core 44. The proximal edge 64 of the barrier means 62 is formed by securing the barrier means element to the topsheet 38 by adhesive 92. The spacing elastic members 77 are enclosed in a tunnel that is formed when an end of the barrier means element is folded back upon itself; the spacing elastic members 77 being secured in the barrier means 62 by elastic attachments means 94. The distal edge 66 of the barrier means is spaced away from the topsheet top surface 40 by the elastic gathering action of the spacing elastic members 77; a channel 96 thereby being formed by at least the proximal edge 64, the distal edge 66 and the inboard surface 68 of the barrier means 62. The channel 96 is shown as being ready to restrain, contain and hold body fluids until the sanitary napkin 210 is removed from the wearer.

The topsheet 38 is compliant, soft feeling, and non-irritating to the wearer's skin. Further, the topsheet 38 is liquid pervious permitting liquids to readily penetrate through its thickness. A suitable topsheet may be manufactured from a wide range of materials, such as porous foams, reticulated foams, apertured plastic films, natural fibers (e.g. wood or cotton fibers), synthetic fibers (e.g. polyester or polypropylene fibers) or from a combination of natural and synthetic fibers. Preferably, it is made of a hydrophobic material to isolate the wearer's skin from liquid in the absorbent core 44.

A particularly preferred topsheet 38 comprises staple length polypropylene fibers having a denier of about 1.5, such as Hercules Type 151 polypropylene marketed by Hercules Inc. of Wilmington. Del. As used herein, the term "staple length fibers" refers to those fibers having a length of at least about 15.9 mm (0.625 inches).

There are a number of manufacturing techniques which may be used to manufacture the topsheet 38. For example, the topsheet 38 may be woven, non-woven, spunbonded, carded, or the like. A useful topsheet 38 is carded, and thermally bonded by means well known to those skilled in the fabrics art. Preferably, the topsheet 38 has a weight from about 18 to about 25 grams per square meter, a minimum dry tensile strength of at least about 400 grams per centimeter in the machine direction and a wet tensile strength of at least about 55 grams per centimeter in the cross machine direction.

The absorbent core 44 may be any means which is generally compressible, conformable, non-irritating to the wearer's skin, capable of absorbing and retaining body fluids. A preferred absorbent core 44 has first and second opposed faces and comprises an absorbent layer 48 and first and second tissue layers 50 and 52, respectively. The first and second tissue layers 50 and 52 overlay the major surfaces of the absorbent layer 48 to form the first and second opposed faces of the absorbent core.

The absorbent layer 48 may be manufactured in a wide variety of sizes and shapes (e.g. rectangular, hour-glass, etc.) and from a wide variety of liquid absorbent materials commonly used in absorbent articles, such as comminuted wood pulp which is generally referred to as airfelt. Examples of other suitable absorbent materials include creped cellulose wadding, absorbent foams, absorbent sponges, super absorbent polymers. or any equivalent material or combination of materials. The total absorbent capacity of the absorbent layer 84 should, however, be compatible with the design body fluid loading in the intended use of the sanitary napkin. Further, the size and absorbent capacity of the absorbent layer 48 may be varied to accommodate wearers.

The dimensions, shape, and configuration of the absorbent layer 48 may be varied (e.g. the absorbent layer may have a varying caliper, or a hydrophillic gradient, or may contain superabsorbent materials or synthetic fibers.

The first and second tissue layers 50 and 52 improve the tensile strength of the absorbent core 44 and reduce the tendency of the absorbent layer 48 to split, lump or ball when wetted. The first and second tissue layers 50 and 52 also help to improve lateral wicking of the absorbed body fluids thereby providing a more even distribution of the body fluids throughout the absorbent layer 48. While a number of materials and manufacturing techniques may be used to manufacture the first and second tissue layers 50 and 52, satisfactory results have been obtained with sheets of tissue paper having a basis weight of about 16 grams per square meter (10 lbs. per 3000 square fee) and having an air permeability of about 30.5 cubic meters per minute per square meter (100 cubic feet per minute per square foot) at a pressure differential of about 12.8 millimeters of water (0.5 inch). While the first and second tissue layers 50 and 52 are preferably coterminous with the absorbent layer 48, they may have different dimensions, a different configuration, or they may be omitted entirely.

The absorbent core 44 is superimposed on the backsheet 42 and is preferably attached thereto by attachments means (not shown) such as those well known in the art. For example, the absorbent core 44 may be secured to the backsheet 42 by a uniform continuous layer of adhesive, a patterned layer of adhesive, or an array of separate lines or spots of adhesive. An adhesive which has been found to be satisfactory is manufactured by Eastman Chemical Products Company of Kingsport, Tenn. and marketed under the tradename Eastobond A-3.

The backsheet 42 is impervious to liquids and is preferably manufactured from a thin plastic film, although other flexible liquid impervious materials may also be used. The backsheet 42 prevents the body fluid absorbed and contained in the absorbent core 44 from wetting articles which contact the sanitary napkin such as undergarments. Preferably, the backsheet 42 is a polyethylene film having a thickness of from about 0.012 mm (0.5 mil) to about 0.051 cm (2.0 mils), although other flexible, liquid impervious materials may be used. As used herein, the term "flexible" refers to materials which are compliant and which will readily conform to the general shape and contours of the human body.

A suitable polyethylene film is manufactured by Monsanto Chemical Corporation and marketed in the trade as Film No. 8020. The backsheet 42 can be embossed and/or matte finished to provide a more clothlike appearance. Further, the backsheet 42 may permit vapors to escape from the absorbent core 44 while still preventing body fluid from passing through the backsheet 42.

The topsheet 38 and the backsheet 42 are associated together in any suitable manner. As used herein, the term "associated" encompasses configurations whereby the topsheet 38 is directly joined to the backsheet 43 by affixing the topsheet 38 directly to the backsheet 42, and configurations whereby the topsheet 38 is indirectly joined to the backsheet 42 by affixing the topsheet 38 to intermediate members which in turn are affixed to the backsheet 42. In a preferred embodiment, the topsheet 38 and the backsheet 42 are joined directly to each other in the periphery by attachment means such as adhesive 88 or any other attachment means as-known in the art. For example, a uniform continuous layer of adhesive, a patterned layer of adhesive, or any array of separate lines or spots of adhesive may be used. The side flap 58 should be highly flexible.

The side flaps 58 are that portion of the sanitary napkin between the periphery and the edges of the absorbent core 44. Thus in an embodiment of the present invention as shown in FIG. 7, the side flaps 58 are formed from the extension of the backsheet 42 and the topsheet 38 from and along the side edges 46 of the absorbent core 44.

Each barrier means 62 is a flexible member having a proximal edge 64, a distal edge 66, an inboard surface 68 and an outboard surface 70. As used herein, the term flexible refers to materials which are compliant and will readily conform to the general shape and contours of the body. In addition, if the spacing means 76 comprise spacing elastic members 77, the barrier means 62 must be contractible so that the distal edge 66 may be sufficiently spaced away from the topsheet top surface 40 so that a channel 96 is formed to restrain, contain and hold body fluids within the article. The barrier means 62 may be manufactured from a wide variety of materials such as , polyester, rayon, nylon, foams, plastic films, formed films, and elastic foams. A number of manufacturing techniques may be used to manufacture the barrier means. For example, the barrier means 62 may be woven, non-woven, carded, or the like. A particularly preferred barrier means 62 comprises a material containing no finish or to render it liquid impermeable. A particularly preferred material is manufactured by Crown Zellerbach Company as Celestra.

As shown in FIG. 7, the barrier means 62, and more particularly the proximal edge 64, is disposed inboard of and preferably adjacent to the flap.

The term "inboard" is defined as the direction toward the center line 36 that is parallel to the respective edge (226, 226') along which the particular barrier means 62 is disposed.

The barrier means 62 is disposed to provide a more effective restraint against the flow of body fluids. The barrier means 62 is preferably disposed between the flap's outer edge and the longitudinal center line 36 of the sanitary napkin.

The proximal edge 64 and the distal edge 66 are in spaced relation to each other and define the width of the barrier means 62. The proximal and distal edges 64 and 66 respectively, may be in a parallel, non parallel, rectilinear or relationship. In addition, the barrier means 62 may have a variety of different cross sectional areas including circular, square, rectangular or any other shape. Preferably, the proximal edge 64 is spaced from the distal edge 66 in a parallel and rectilinear relationship to provide a barrier means 62 having uniform widths.

The embodiment of the sanitary napkin shown in FIG. 7 is provided with the barrier means 62 joined to the topsheet 38. The term "joined" includes any means for affixing the barrier means 32 to the sanitary napkin and includes embodiments wherein the barrier means 62 is a separate element having the proximal edge 64 directly or indirectly attached to the topsheet 38 (i.e. integral) or embodiments wherein the barrier means 62 is made from the same element or material as the topsheet 38 so that the proximal edge 64 is a continuous and undivided element of the topsheet (i.e. unitary). The barrier means 62 may alternatively be joined to the side flap 58, the backsheet 42, the absorbent core 44, the topsheet 38 or any combination of these or other elements of the sanitary napkin. In the embodiment as shown in FIG. 7, the barrier means 62 are integral with the topsheet 38. The integral barrier means 62 is preferably formed by a single strip of material which is secured to the topsheet by adhesive 92, the distal edge 66 being formed by folding an end of the material back upon itself.

The distal edge 66 is preferably disposed inboard of the proximal edge 64 a present a more effective barrier against the flow of . The distal edges 66 are maintained inboard of the proximal edges 64 by the adhesive means 78 so as to obviate their inversion. While the distal edges 66 may alternatively be disposed in other positions in relation to the proximal edges 64, such positions are not preferred.

The distal edge 66 is preferably not secured to any other element in at least a centre region of the sanitary napkin so that it may be spaced away from the top surface 40 of the topsheet 38. The distal edge 66 is preferably spaced away from the top surface 40 of the topsheet 38 so that the barrier means 62 may form a channel 96 to enhance the containment of the article. As used herein, "spaced" includes embodiment wherein the distal edges 66 may assume one or more positions relative to the top surface 40 of the topsheet 38 including at some times assuming a position adjacent the top surface 40 of the topsheet 38. The distance between the distal edge 66 to the top surface 40 of the topsheet 38 is measured along a line drawn from the distal edge 66 to the closest part of the topsheet 38 when the distal edge 66 is positioned so as to be spaced away from the topsheet as far as possible, (i.e. in the contracted position). Preferably, the distal edge 66 is spaced away from the topsheet 38 by a height of at least about 2 mm, and more preferably of from about 5 mm to about 10 mm.

The channel 96 is formed at least along the proximal and distal edges 64 and 66 and the inboard surface 68 of the barrier means 62. The channel 96 forms a barrier to the flow of bodyfluid as they tend to move across the topsheet 38.

The barrier means 62 may additionally be provided with absorbent means secured to or within the barrier means 62. The absorbent means absorb and contain body fluid which contact the barrier means 62. The absorbent means may be any means which is capable of absorbing and retaining liquid and may have any size, shape, configuration or absorbent capacity. The absorbent means may be positioned to the barrier means 62 along the inboard surface 68 or within the barrier means 62. Preferably, the absorbent means is a layer of airfelt secured within the tunnel formed by the integral barrier means and secured along the entire length and width of the inboard surface 68 of the barrier means 62.

In addition, the barrier means 62 may be rendered liquid impermeable so as to prevent the of bodyfluid. A liquid impermeable barrier means 62 retards the movement of liquid through the barrier means 62, thereby making it more leakage resistant. The barrier means 62 may be rendered liquid impermeable in any manner well known in the art such as selectively treating the barrier means, the barrier means, or by securing a separate material to the barrier means.

The spacing means 76 for spacing the distal edge 66 away from the topsheet top surface 40 is any member which gathers, contracts, stiffens, shortens or otherwise acts on the barrier means 62 so as to cause a channel 96 to be formed along the barrier means 62 to provide a constraint against the leakage of.

As shown in FIG. 7 the spacing means 76 preferably comprise spacing elastic member 77 secured adjacent the distal edge 66 inside of the barrier means 62. The spacing elastic member 77 is preferably secured to the barrier means 62 in an contractible condition so that in a normally unrestrained configuration,, the spacing elastic member 77 effectively contracts or gathers the barrier means 62.

As shown in FIG. 7, the spacing elastic member 77 is associated with the barrier means 62 by securing it within the barrier means with elastic attachment means 94. While the spacing elastic members 77 may be secured to the barrier adjacent only the ends of the elastic spacing member 77, it is preferable to secure the entire length of the spacing elastic member 77 to the barrier means 62. The elastic attachment means 94 herein are preferably glue beads made of hot melt adhesive such as marketed by Adhesives Incorporated, Wis., as Adhesives 581.

A spacing elastic member 77 which could be suitable is an elastic strand having a cross section of 0.18 mm by 1.5 mm and made from natural rubber as available from Rubber Company of, Va., under the trademark L-1900 Rubber Compound. Other suitable spacing elastic members 77 can be made from natural rubber, such as elastic tape sold under the trademark 9211 by Company of Scotland. N.C. The spacing elastic member 77 may also comprise any heat shrinkable elastic material as is well known in the art. Other suitable elastic materials may comprise a wide variety of materials as are well known int he art include films, polyurethane films, foams and formed elastic.

In addition, the spacing elastic members 77 may take a multitude of configurations. For example, the width of the spacing elastic members 77 may be varied; the spacing elastic members may comprise a single strand or several parallel or non-parallel strands of elastic material; or the spacing elastic members 77 may be rectilinear or curvilinear. Still further, the spacing elastic members 77 may be affixed to the barrier means 62 in any of several ways which are well known in the art. For example, the spacing elastic members 77 may be bonded or heat sealed into the barrier means 62 using a variety of bonding patterns, or the spacing elastic members 77 may simply be glued to the barrier means 62.

The spacing means 76 for spacing the distal edge 66 away from the topsheet top surface 40 may alternatively comprise several other elements. For example, the barrier means 62 may have stiffening means disposed in or on each barrier means 62. The stiffening means must be sufficiently stiff so that the distal edge 66 is spaced away from the topsheet top surface 40. Suitable materials for the stiffening means include foams, fabrics, batting, polyethylene film formed films, spray glues, foamed polyester, or a high loft material as is manufactured by Carolina Formed Fabrics.

The spacing means 77 may also comprise means for shortening the length of the distal edge 66 in comparison to the length of the edges of the sanitary napkin. The distal edge 66 can be shortened by making a fold or pleat in the distal edge 66. This fold or pleat is secured by any of the holding means well known to those of ordinary skill in the art, such as adhesives or heat sealing. Alternatively, a section may be cut out of the distal edge and the edges brought together to form a butt or joint. The distal edge 66 may also be shortened by attaching a length of the distal edge 66 to the topsheet 38 at a position different from where the distal edge 66 would lie when the sanitary napkin is in a flattened out condition. Other shortening techniques as are known in the art may also be used.

The adhesive means for securing end portions of the barrier means 62 closed near the lateral edges of the sanitary napkin provide a more comfortable fit for the wearer and obviate inversion of the distal edges 66 of the barrier means 62 during application and use. Inversion is generally defined as the inboard disposed distal edge 66 turning outwardly when the sanitary napkin is applied to the wearer. In a preferred embodiment such adhesive means are disposed in the front region and the back region of the sanitary napkin. The remaining portions of the barrier means 62 are not secured closed so that the distal edges 66 are left freely.

The adhesive means 78 are preferably glue beads 79 consisting of hot melt adhesives such as marketed by Adhesives Incorporated, Wis., as Adhesives 581.

It is claimed:

1. A sanitary napkin of the type for placement in an undergarment, the sanitary napkin comprising:
   (a) a central absorbent pad having a pair of longitudinal edges, a body contacting surface, a central region, and a pair of ends, said central absorbent pad comprising:
      a liquid pervious topsheet;
      a liquid impervious backsheet joined with said topsheet; and
      an absorbent core positioned between said topsheet and said backsheet;
   (b) a flap extending outwardly from each longitudinal edge of said central absorbent pad in said central region, each said flap being joined with said central absorbent pad and being sized and configured to allow each of said flaps to be positioned around the edge of an undergarment at a flexible axis; and
   (c) barrier means for restricting liquid migration in the general direction of the lateral sides, each said barrier means comprising:
      a barrier element having
      a proximal edge joined to said flap, and
      a free edge spaced from said proximal edge and being free from securement to at least a portion of said flap or said central absorbent pad.

2. The sanitary napkin of claim 1 wherein said backsheet of said central absorbent pad extends to said flap and forms a portion of a flap backsheet for said flaps.

3. The sanitary napkin of claim 2 wherein said proximal edge is joined to said flap backsheet.

4. The sanitary napkin of claim 3 wherein said topsheet of said central absorbent pad extends to said flaps and forms a portion of a flap topsheet for said flaps.

5. The sanitary napkin of claim 4 wherein each said barrier element is liquid impermeable.

6. The sanitary napkin of claim 5 wherein said free edge of said barrier element is inboard of said proximal edge.

7. The sanitary napkin of claim 6 wherein said free edge is positioned over said absorbent core.

8. The sanitary napkin of claim 2 wherein said topsheet of central absorbent pad extends to said flaps and forms a portion of a flap topsheet for said flaps.

9. The sanitary napkin of claim 8 wherein said proximal edge is joined to said flap topsheet.

10. The sanitary napkin of claim 8 wherein said barrier element is a unitary construction with said flap topsheet.

11. The sanitary napkin of claim 1 wherein said absorbent core has side edges, and each said proximal edge is joined to said flap between said flexible axis and a side edge of said absorbent core.

12. The sanitary napkin of claim 11 wherein each said flap additionally has a second flexible axis allowing said flap to bend upwardly between said flexible axis and said second flexible axis, each said proximal edge being joined to said flap between said second flexible axis and a side edge of said absorbent core.

* * * * *